United States Patent [19]
Ling et al.

[11] 3,939,496
[45] Feb. 24, 1976

[54] ENDOPROSTHETIC BONE JOINT

[75] Inventors: Robin Sydney Mackwood Ling, Teignmouth; Alan John Clive Lee, Exeter, both of England

[73] Assignee: National Research Development Corporation, London, England

[22] Filed: Oct. 2, 1974

[21] Appl. No.: 511,264

[30] Foreign Application Priority Data
Oct. 15, 1973   United Kingdom............... 47961/73

[52] U.S. Cl...................... 3/1.91; 3/1.911; 128/92 C
[51] Int. Cl.².......................................... A61F 1/24
[58] Field of Search........................ 3/1.9–1.912, 3/22, 1; 128/92 C, 92 R

[56] References Cited
UNITED STATES PATENTS
3,696,446   10/1972   Bousquet et al..................... 3/1.911

FOREIGN PATENTS OR APPLICATIONS
163,476   6/1958   Sweden............................. 128/92 C OTHER PUBLICATIONS
Original Gschwend Total Elbow, advertisement by Promed International Inc., *The Journal of Bone & Joint Surgery*, Vol. 55-A, No. 3, Apr. 1973.
"Arthroplasty of the Knee," by L.G.P. Shiers, The *Journal of Bone & Joint Surgery*, Vol. 36B, No. 4, Nov. 1954, pp. 553–560.
McKee Finger Joints – No. 6949, *Vitallium Surgical Appliances* (catalog) Austenal Medical Div. Howmet Corp. New York, N.Y., 1964, p. 53.

*Primary Examiner*—Ronald L. Frinks
*Attorney, Agent, or Firm*—Cushman, Darby & Cushman

[57] ABSTRACT

An endoprosthetic bone joint device developed for the elbow, but applicable elsewhere, has two hinge components respectively defining complementary first and second bearing surfaces for mutual articulatory engagement, and each apertured to define third bearing surfaces. When implanted the hinge components are first coupled by a further component passed through the apertures and defining fourth bearing surfaces to articulate with the third surfaces. At this stage all of the bearing surfaces are appropriately engaged and stabilization of the implantation securement is facilitated. Subsequently the coupling can be removed to reduce the effect of distraction stresses on the device. The first and second surfaces are suitably of spherical ball and socket form, and can be of a twinned form, while the third and fourth surfaces are suitably of circular cylindrical form extending diametrally through the ball and socket.

4 Claims, 2 Drawing Figures

U.S. Patent  Feb. 24, 1976  3,939,496
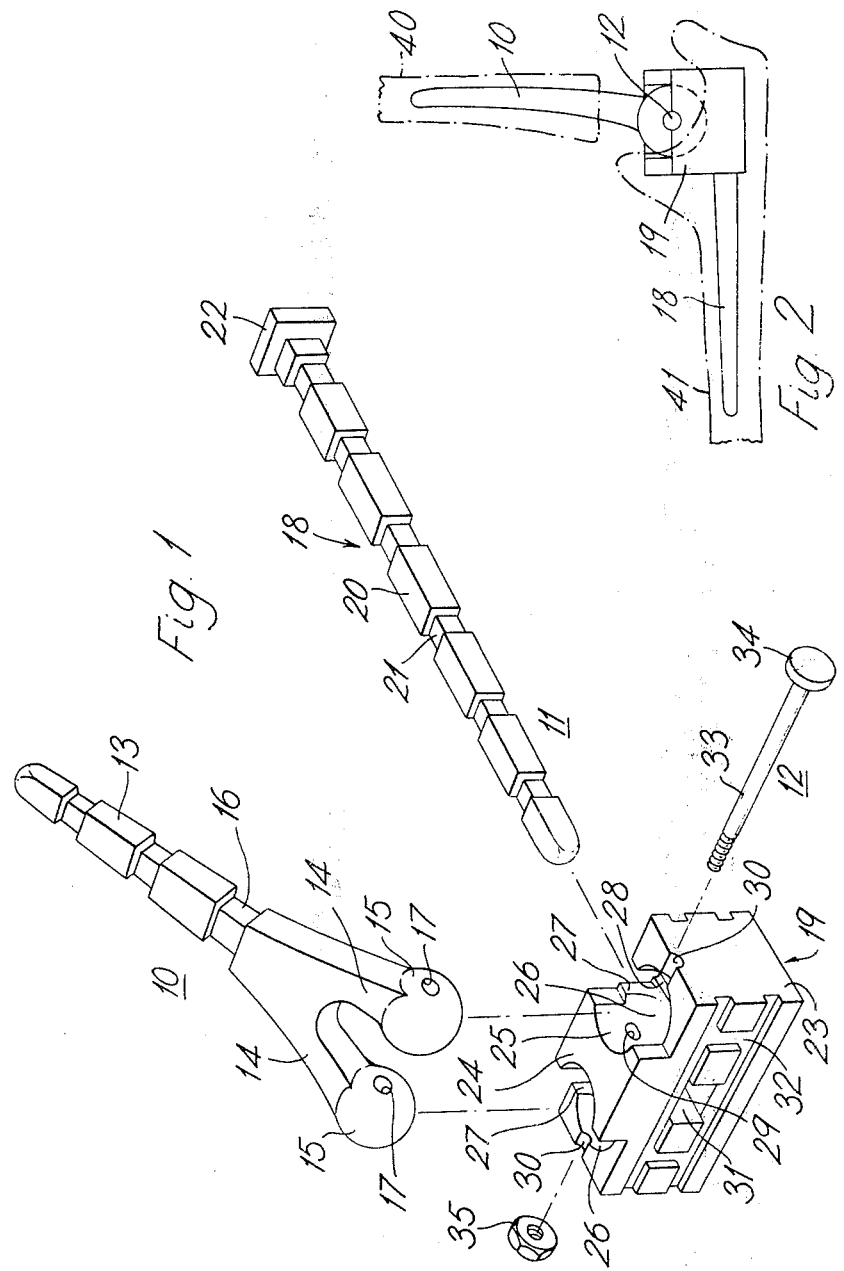

ENDOPROSTHETIC BONE JOINT

This invention concerns endoprosthetic devices and more particularly such devices for replacing the articulatory function of bone joints. The invention has in fact been developed in relation to the elbow joint and will be described hereinafter in this context, but it is to be understood that, in a broader aspect, the invention is applicable to other joints.

The commercially available endoprosthetic elbow joint devices conventionally involve a directly coupled hinge structure comprising separate humeral and ulnar components and a coupling pivot pin which co-operates with each of the former components in bearing enegagement to provide articulation by rotation of the components about the longitudinal axis of the pin. However, while the results with such devices have proved generally satisfactory to date, recent evidence suggests that these devices may be subject to disadvantage in the longer term. More specifically, it appears that distraction stresses which are transmitted through the pivot pin to both of the associated hinge components can weaken the securement of these components in their respective bones. Such securement normally involves the use of intramedullary stems and acrylic resin cement as gap-filling medium, and the bond between such cement and the bone is particularly unsuited to withstanding the tensile stresses and, to a lesser degree, torsional stresses which result from distraction.

An object of the present invention is to reduce the difficulties of this situation and accordingly provides an endoprosthetic bone joint comprising: two hinge components and a hinge-coupling component; said hinge components being adapted for fixation to respective bones of the relevant joint, respectively having first and second bearing surfaces of complementary form for mutual articulatory bearing engagement, and having apertures to provide respective third bearing surfaces of mutually similar form; and said hinge-coupling component having a fourth bearing surface of complementary form to said third bearing surfaces, and being adapted for releasable receipt in said apertures to couple said hinge components and maintain said first and second, and said third and fourth, bearing surfaces in mutual articulatory engagement.

The first and second bearing surfaces will normally be of respective ball and socket forms, and the third and fourth bearing surfaces of respectively concave and convex cylindrical forms extending diametrically through the former. Also, twinned ball and socket surfaces with the cylindrical surfaces extending along a common diameter of the former are possible.

In use of the invention the components are implanted to provide a directly coupled hinge assembly, but after an initial post-operative period during which healing is completed and the two hinge components become stabilized within the capsule of the natural joint, the coupling component is removed by relatively minor surgery. Thereafter the two hinge components serve as a hinge assembly to provide the required articulatory function through the mutual engagement of their first and second bearing surfaces, but the components are indirectly coupled by way of the bones and capsule so that any transmission of distraction stresses through the hinge assembly is significantly reduced.

For a fuller understanding of the invention, the same will now be described by way of example with reference to the accompanying drawings, in which:

FIG. 1 diagrammatically illustrates in an exploded perspective view one embodiment of a prosthetic elbow joint device according to the invention; and FIG. 2 diagrammatically illustrates the device of FIG. 1 in side elevation, assembled form, and in relation to an ulna and humerus to which the device is secured.

The illustrated device comprises a humeral component 10 and a two-part ulnar component 11, which components serve as the afore-mentioned hinge components, and a hinge-coupling component in the form of a pin 12.

The humeral component 10 comprises an integral structure of tapered intramedullary stem 13 which is forked at its wider end to provide two arms 14 terminating at their respective ends in like spherically shaped bearing members 15. The stem 13 is of substantially rectangular cross-sectional shape and tapered in both lateral aspects towards its free end, which is rounded. Also, the stem 13 has a relieved surface formation by the provision of annular grooves 16 therearound at successively spaced locations along the length of the stem.

The more general geometry of the humeral component is symmetrical about the longitudinal medial plane thereof passing between the arms 14, while the component is curved, at least over its wider ends including the arms 15, in an orthogonal longitudinal plane as seen in FIG. 2.

It is to be noted that, at least in planes parallel to the afore-mentioned medial plane, the bearing members 15 have a diameter greater than the cross-sectional dimensions of the adjoining arms 14, so that the spherical surfaces of the bearing members subtend angles greater than 180° in such planes. Also, the bearing members are apertured by the provision of respective diametral bores 17 therethrough perpendicularly to said planes.

Turning to the ulnar component 11: this is of two-part form comprising a shaft 18 and a bearing block 19. The shaft 18 serves over its major length as an intramedullary stem 20 and is similar to the humeral component stem 13 in being of substantially rectangular cross-sectional shape, doubly tapered towards a rounded free end, and provided with annular grooves 21 therearound at successively spaced locations along its length. The remaining minor end portion of the shaft 18 is in the form of an end cap 22 also of substantially rectangular form.

The bearing block 19 has a first body portion 23 of substantially rectangular form with a similarly shaped second body portion 24 upstanding from the longitudinally central area of one side face of the body portion 23, so that the block 19 has an overall inverted T-shape of which the portions 23 and 24 respectively constitute the cross-bar and stem. The block is further shaped by the formation of two concave recesses, respectivaly located in the angled regions between the two undersurfaces of the cross-bar body portion 23 and the adjacent side faces of the stem body portion 24. These recesses each comprise a semi-circular cylindrical portion 25 extending along the stem body portion 24 to lead smoothly into a spherical portion 26 in the cross-bar body portion 23. The spherical portions 26 are of like diameter and mutual spacing as the humeral components' bearing members 15 with which they are complementary, but the former are of lesser extent, namely, not greater than hemispherical. This complementary relationship is extended by the provision of two further recesses 27 to respectively communicate the spherical recess portions 26 with a common side face of the cross-bar body portion 23, and these further recesses are, in their relationship with the portions 26, generally complementary to the convexly curved portions of the arms 14 adjoining the humeral component bearing member 15.

Further features of the bearing block 19 comprise channels 28 leading from the base of the spherical recess portions 26 to the outer edge of the recesses 27; a bore 29 extending through the stem body portion 24 along the common diametral direction with respect to the spherical recess portions 26, and semi-cylindrical extensions 30 of the bore 29 which extensions are disposed in the cross-bar body portion 23; a passageway 31 passing through the cross-bar body portion 23 orthogonally to the bore 29; and mutually perpendicular grooves 32 formed in the side faces of the body portion 23. The bore 29 is of like diameter with the humeral component bore 17, and is fully exposed from the ends of the bearing block by the associated semi-cylindrical extensions 30. The passageway 31 is of doubly-tapered, rectangular form complementary to the end portion of the ulnar component stem 20 adjoining the associated end cap 22, the passageway 31 being tapered from its end adjacent the bearing block recesses 27. The grooves 32 extend parallel with the principal dimensions of the respective side faces and the passageway 31 opening thereinto, and at the wider end of this passageway the grooves circumscribe the same to form a recess complementary to the ulnar component shaft end cap 22.

The hinge-coupling pin 12 has a cylindrical shaft 33 of like diameter to the bores 17 and 29 in the other components, terminates at one end in a head 34, and is screw-threaded at its other end for connection with a nut 35.

Lastly concerning the form of the illustrated components: it is presently preferred that these be made of a metal, such as a suitable chromium-cobalt-molybdenum alloy, except for the bearing block 19 which is to be of a suitably compatible plastics material, such as high density polyethylene.

In use of the illustrated device the distal end of the humerus is suitably sectioned and the exposed medullary canal reamed for securement of the humeral component stem 13 therein in association with acrylic resin cement or equivalent gap-filling medium. The double taper of the stem 13 is beneficial in effecting extrusion of cement therearound into the cancellous bone bordering the canal, and the grooves 16 are further beneficial in keying the cement with the stem. The general disposition of the humeral component 10 when secured in the humerus is indicated by FIG. 2 in which the humerus is denoted at 40.

The ulnar component is secured in the proximal end of the ulna of which the head is excavated to receive the bearing block 19 and the exposed medullary canal reamed to receive the stem 20 of shaft 18. Again use is made of acrylic resin cement to secure the bearing block and also the shaft. The resultant general disposition relative to the ulna, which is denoted at 41, is indicated by FIG. 2, the block 19 being located with its side face incorporating the wider end of passageway 30 exposed in the end aspect of the ulna and the recess portions 25 and 26 also exposed.

Assembly of the components involves location of the spherical bearing members 15 of the humeral component in articulatory bearing engagement with the spherical recess portions 26 of the ulnar component by way of the associated cylindrical recess portions 25. This engagement is of a pivotal articulatory nature with the pivotal axis being the common diameter of the relevant spherical surfaces. Also, this engagement serves to align the bores 17 and 29, 30 of the humeral component and ulnar bearing block, and the engagement is stabilized, as a temporary measure, by passage of the coupling pin 12 through the aligned bores and securement of the pin with nut 35. This coupling affords a secondary articulatory engagement of a pivotal form and for which the pivotal axis is the longitudinal axis of the pin. Since the pin axis lies along the common diameter of the above-mentioned spherical surfaces, the two articulatory capabilities are coaxial and the first-mentioned of these is maintained while the device is stabilized by the coupling pin. The recess 27 serves to receive the arms 14 and allow a greater range of pivotal movement for the humeral component 10 in one direction then the other relative to the bearing block 19, while the channels 28 allow drainage of debris.

While the present invention has been described with more particular reference to the illustrated embodiment, it is clearly open to variation within the more general discussion thereof in the introductory passage hereinbefore. For example, the illustrated embodiment involves an effectively duplicated spherical bearing assembly, whereas a relatively simple singular form can be employed, or a relatively more complex singular form can be employed by integrating the duplicated bearing surfaces into a saddle configuration. Also, while use is made of spherical bearing surfaces, the natural articulatory function to be replaced is almost entirely a single pivotal freedom of movement, and bearing surfaces of generally cylindrical form can be employed to afford an appropriate hinging action.

Further variation can be made in the form of the ulnar component. This component is preferably of the illustrated two-part form since this requires a reduced amount of bone removal from the ulna compared to a more conventional form of component with integrated bearing part and stem, and also allows the bearing block 19 to be laterally embraced within the ulna except for receipt of the separate shaft 18. However, an integrated ulnar component can be employed with the present invention.

Lastly, it has been mentioned initially that the invention is applicable to other bone joint prostheses, and such application is clearly appropriate to other joints such as the knee where the principal articulation is hinge-like.

We claim:
1. An endoprosthetic bone joint device comprising:
a first hinge component of forked form with two form arms similarly defining at their free end portions respective spherically-shaped ball bearing surfaces, and said arms being diametrally bored relative to said ball surfaces to define respective, coaxially aligned, concave, circular cylindrical bearing surfaces therethrough;
a second hinge component including a bearing part of generally T-shape with a cross-bar and stem, said cross-bar similarly defining at its free end portions respective spherically-shaped socket bearing surfaces in articulatory engagement with said ball surfaces, and said stem being bored to define a further concave circular cylindrical surface coaxially aligned with, and disposed between, the first-mentioned concave surfaces; and a hinge-coupling component defining a convex circular cylindrical surface located in articulatory engagement with said concave surfaces, said hinge-coupling component being releasably connected with said hinge components.

2. A device according to claim 1 wherein said second component is of two-part construction comprising said bearing part and an elongate intramedullary fixation member, said bearing part having a passageway extending generally orthogonally therethrough relative to said T-shape cross-bar and stem, said fixation member being releasably located in said aperture to extend from one side of said bearing part.

3. The use of an endoprosthetic bone joint device, which device comprises:

two hinge components adapted for fixation to respective bones of the relevant joint, respectively having first and second bearing surfaces of complementary form, and having apertures to provide respective third bearing surfaces of mutually similar form; and a hinge-coupling component having a fourth bearing surface of complementary form to said third bearing surfaces, and being releasably locatable in said apertures to hold both said first and second surfaces, and said third and fourth surfaces, in respective mutual articulatory engagement;

and which use comprises:

implanting said hinge components with said hinge-coupling component located in said apertures, and then, after a period of time during which such implantation becomes stabilized, removing said hinge-coupling component.

4. The use of an endoprosthetic elbow joint device, which device comprises an ulnar component of two-part construction including a bearing part having a passageway therethrough, and an elongate intramedullary fixation member releasably locatable in said passageway to project from one end thereof, and which use comprises excavating the proximal end of the ulna and reaming the medullary canal exposed thereby to respectively receive said bearing part and fixation member, locating said bearing part in the excavated ulna, and then passing said fixation member through said passageway and into said reamed canal to secure said component.

* * * * *